United States Patent [19]

Prussin et al.

[11] 3,966,090
[45] June 29, 1976

[54] PACKAGE FOR DISPENSING AN ANTISEPTIC COMPOSITION

[75] Inventors: Samuel B. Prussin; Davis S. Lozano, both of Los Angeles, Calif.

[73] Assignee: Dart Industries Inc., Los Angeles, Calif.

[22] Filed: June 19, 1972

[21] Appl. No.: 263,807

Related U.S. Application Data

[63] Continuation-in-part of Ser. No. 799,978, Feb. 17, 1969, abandoned.

[52] U.S. Cl. .............................. 222/94; 222/192; 424/43; 424/45
[51] Int. Cl.² ................ A61K 33/18; B65D 35/22
[58] Field of Search ............ 222/192, 94, 194, 129, 222/146 HA; 424/47, 130, 150, 43, 45

[56] References Cited

UNITED STATES PATENTS

| | | | |
|---|---|---|---|
| 2,941,696 | 6/1960 | Homm | 222/136 |
| 2,973,883 | 3/1961 | Modderno | 222/94 |
| 3,217,936 | 11/1965 | Abplanalp | 222/136 |
| 3,248,281 | 4/1966 | Goodenough | 167/17 |
| 3,272,389 | 9/1966 | Frangos | 222/136 |
| 3,295,727 | 1/1967 | Kates et al. | 222/136 |
| 3,341,418 | 9/1967 | Moses et al. | 167/85 |
| 3,490,651 | 1/1970 | Abplanalp | 222/94 |
| 3,632,516 | 1/1972 | Antonelli et al. | 222/146 HA X |

OTHER PUBLICATIONS

Jacobson et al., Encyclopedia of Chemical Reactions, p. 532 (1953).

Primary Examiner—V. D. Turner
Assistant Examiner—Allen J. Robinson
Attorney, Agent, or Firm—Kenneth J. Hovet

[57] ABSTRACT

Packages are described wherein two compositions are maintained isolated from each other within a container, the first composition comprising a substance capable of releasing iodide ion and the second composition comprising hydrogen peroxide. The container is fitted with valve means which communicate with each composition. Actuation of the valve means results in mixing portions of each composition and dispensing of the mixture as a composition containing iodine.

5 Claims, No Drawings

PACKAGE FOR DISPENSING AN ANTISEPTIC COMPOSITION

This is a continuation-in-part of application Ser. No. 799,978 filed Feb. 17, 1969 now abandoned.

This invention relates to packages adapted to the dispensing of an antiseptic composition containing free iodine.

Iodine is a well-known substance which has marked antiseptic properties and has many uses as a disinfectant. One of the problems associated with the use of iodine as an antiseptic for human skin is the fact that it tends to cause unsightly brown discoloration when applied to the skin. Without this effect, iodine would have marked advantages in such uses as cleaning the hands of a surgeon prior to operative procedures, in treatment of acne and dandruff and in general antiseptic uses. The consept of packaging a wide range of products in pressurized containers where the product is dispensed in aerosol form has been widely accepted, particularly in recent years. The preparation of an aerosol form of iodine presents specific problems due to the corrosive nature of iodine.

The invention sought to be patented resides in the concept of a package with means to maintain two compositions isolated from each other within the package, one of said compositions comprising an alkali metal iodide and the other of said compositions comprising hydrogen peroxide and valve means communicating with each composition whereby the application of pressure to the compositions and actuation of the valve means results in the mising of portions of each composition and dispensing of the mixture from the package in a form suitable for direct application to the skin with antiseptic properties due to the presence of free iodine.

The alkali metal iodide and hydrogen peroxide should be present in amounts sufficient to produce a free iodine concentration in the dispensed product of about 0.5 – 5.0 percent. Any stronger concentrations would generally be impractical and would not result in any substantial improvement in disinfectant qualities.

The manner and process of making and using the invention will now be described generally so as to enable one skilled in the art of cosmetic chemistry to make and use the same as follows:

Packages within the scope of the invention are in the form of a container filled with two compositions which are maintained isolated from each other. One of these compositions comprises an alkali metal iodide, for example, potassium iodide or sodium iodide, or one of its hereinafter described equivalents. The concentration of the iodide will range from 2 – 50 percent by weight of the product and will be present within the package in liquid form as a solution in water or other appropriate solvent. The composition can also include less than about 1.0% of a catalyst such as a alkali metal molybdate to accelerate the conversion of iodide to free iodine.

The other composition which is maintained in the package isolated from the alkali metal iodide composition comprises hydrogen peroxide or one of its hereinafter described equivalents. This composition is also present as a liquid phase, for example, as a solution of hydrogen peroxide in water or preferably an emulsified system in the presence of surfactants such that the mixture dispensed from the package will be in the form of a foam in which the antiseptic action of the liberated iodine is enhanced by the presence of the surfactant.

This composition will include conventional stabilizers and preservatives to maintain the hydrogen peroxide in an environment such that it will not decompose. Compositions with surfactant have the added advantage of causing no staining of the skin. The relative proportions of hydrogen peroxide to alkali metal iodide in packages of this invention should be sufficient at least for the oxidation of iodide ion to free iodine. This, of course, will vary and will be proportionately increased when a warmed product is desired. Generally, a range of about 2 to 30 percent hydrogen peroxide will be satisfactory.

A particular advantage of the iodine-containing compositions dispensed from packages of this invention is that controllable heat may be evolved. The compositions may thus be dispensed in a warmed state. This improves the efficiency of cleaning and antiseptic action of such compositions.

As described above, the two compositions are maintained isolated from each other within a container. Such a container is constructed of rigid or flexible material, depending upon the pressurization means to be utilized for dispensing. A collapsible container formed of plastic or metal is used where pressurization is effected manually by squeezing. In accordance with a preferred embodiment of this invention, self-pressurization is employed through use of a liquefied propellant gas within the container in either or both of the isolated compositions and, in this case, a pressure-tight container having sufficient wall strength to withstand the propellant pressure is employed. The container can be formed of a wide class of materials used in the art of aerosol packaging such as glass, rigid plastics and metal. Such propellants must be of such a nature that they are compatible with the compositions in which they are included. Such propellants should have a vapor pressure of approximately 12 to 85 pounds per square inch gauge at 70°F. using as propellants saturated aliphatic hydrocarbons such as propane, butane, isobutane, and the like, and/or chlorofluoralkanes containing not more than two carbon atoms and at least one fluorine atom having the desired vapor pressure for use in the invention. Propellant gasses such as nitrogen, carbon dioxide or nitrous oxide or liquefied propellants such as dimethyl ether with a high degree of water solubility may also be used as pressurization means. Mixed propellant systems can also be employed, for example, a mixture of dimethyl ether and a chlorofluoralkane or hydrocarbon, or a hydrocarbon or chlorofluoroalkane in combination with a gas which is inert to the system such as nitrogen or carbon dioxide.

The two compositions, formulated as described above, are packaged within a container in such a way as to remain isolated from each other. Valve means are provided to communicate with each composition such that, upon actuation of the valve means, a quantity of each composition is mixed and the resulting mixture is dispensed from the package. It is apparent that the concentration of the respective ingredients must be adjusted in relation to the proportioning properties of the valve means such that a proper mixture of the two compositions based upon the desired end use, results from actuation of the valve means. It is to be understood that the present invention provides for free iodine concentration in the end product of from about 0.5 to 5.0 percent by weight of the total product. This is far greater than the prior art shows and gives a particular advantage where skin antisepsis must be insured, e.g., in surgical scrubs. In accordance with preferred aspects of the present invention the iodine content, for any given temparature, may be raised or lowered by raising or lowering the alkali metal iodide content by between about 2.6 and 2.8 parts, and the peroxide content by between 0.2 and 0.25 parts for each percent the iodine content of the end product is to be raised or lowered.

There are many different ways in which the final package can be constructed in accordance with this invention which will influence the selection of appropriate valve means and the means selected for pressurization. Several such ways are discussed hereinafter.

The package can be constructed in the form of a two-chambered container, separated by a rigid wall, with each chamber fitted with a valve leading to a common discharge conduit. Such a structure is illustrated in U.S. Pat. No. 2,941,696 and with this type of package both compositions are pressurized. Alternately, structure as illustrated in U.S. Pat. No. 3,295,727 can be employed, in which case one of the compositions is pressurized and is present in the body portion of the container with the second composition in the illustrated chamber surrounding the dip tube. The vapor pressure of the first composition bears upon the second composition in this structure and both are dispensed upon valve actuation. U.S. Pat. No. 3,272,389 illustrates another form of package construction useful in the invention. In this structure, venturi action of the pressurized composition within the container provides the motive force for dispensing the second composition.

A particularly desirable form of package for use in accordance with the invention is to utilize a package having two compartments in which the two compositions are packaged within a pressure-tight container, the compartments being separated by a movable wall actuatable upon a pressure differential between the two compartments when the valve means affixed to the container are actuated. The composition within the container outside the movable wall is pressurized. In such a system, the movable wall can be in the form of a movable piston, for example, as illustrated in U.S. Pat. No. 3,217,936 or in the form of a collapsible bag as illustrated in U.S. Pat. No. 2,973,883.

The disclosures of all of the aforementioned patents are incorporated by reference herein for illustrative purposes to the same extent as if set forth at length herein. It is to be understood that such patents are merely illustrative of various means to package the two compositions of this invention within a container and to dispense portions of both compositions to insure mixing and dispensing upon actuation of the valve means.

Packages of this invention are filled by conventional means. Where pressurization is brought about by a liquefied propellant included in either or both compositions, filling can be by either pressure- or cold-filling techniques.

This invention has been described with specific reference to hydrogen peroxide as the oxidizing agent and to alkali metal iodides as the source of iodide ion which is converted to free iodine during the dispensing of packages in accordance with this invention. Other peroxygen compounds such as organic and inorganic peroxide in the preparation of packages of the invention. It will also be apparent that other sources of iodide ion than alkali metal iodides are available, for example, ammonium and amine iodides, other metal iodides and quaternary iodide salts, and such substances are the full equivalents of alkali metal iodides in the preparation of packages of this invention.

The two compositions can be formulated with added ingredients conventional in antiseptic compositions for topical application, for example, humectants and fragrances to yield a product dispensed from the package with the desired degree of elegance. The hydrogen peroxide composition may contain emulsifiers where insoluble propellants and a multi-phase emulsion system are utilized. Alternately, with inert gas pressurization, soluble propellants, or a two-liquid phase system, the hydrogen peroxide composition can consist solely of an aqueous acid solution of hydrogen peroxide with a suitable stabilizer.

The best mode contemplated by the inventors for carrying out their invention will now be set forth as follows:

EXAMPLE I

The following compositions are utilized to prepare a package of the form illustrated in U.S. Pat. 2,973,883:

A. HYDROGEN PEROXIDE COMPOSITION

| | Parts by Weight |
| --- | --- |
| Lanolin Oil | 3.937 |
| Polyoxyethylene (23) Laryl Alcohol Ether | 1.185 |
| Light Mineral Oil | 10.245 |
| Polyoxyethylene Sorbitan Monolaurate | 7.875 |
| Glyceryl Monostearate | 3.150 |
| Stearic Acid | 4.725 |
| Ethylene Oxide Ether of Cholesterol (24 Mole) | 2.370 |
| Water | 17.213 |
| Phenacetin | 0.225 |
| 35% Hydrogen Peroxide | 24.075 |
| | 75.000 |

| B. ALKALI METAL IODIDE COMPOSITION | Parts by Weight |
| --- | --- |
| Water | 20.00 |
| Potassium Iodide | 5.00 |
| | 25.00 |

Fill 75 parts by weight of Composition A into a pressure-tight container. Fill a collapsible container having a diameter smaller than the opening in the pressure-tight container with 25 parts by weight of Composition B. Insert collapsible container and affix valve means to communicate individually with the two compositions, the valve means being constructed such that actuation causes flow of Compositions A and B in the relative proportions of 3:1. Pressurize container with 4.5 parts by weight of a mixture of 84% isobutane 16%-propane. Actuation of the valve means results in the mixing of portions of the two compositions to yield a rich, brown iodine-containing foam with efficaceous antiseptic properties which is dispensed in a warmed state. Washing the skin with water after application results in a total absence of a brown stain.

EXAMPLE II

A package is prepared in accordance with the procedure of Example I using the formulations of Example I except that Composition B is modified by the addition of 0.025 parts by weight of sodium molybdate. An iodine-containing rich, brown foam is produced upon valve actuation.

EXAMPLE III

The following ingredients in the proportions indicated are heated to 75°C., mixed with stirring and cooled to room temperature with stirring:

A. HYDROGEN PEROXIDE COMPOSITION

| | Parts by Weight |
|---|---|
| Stearic Acid | 11.20 |
| Coconut Oil Fatty Acids (primarily 12–16 carbon atoms) | 2.25 |
| Polyoxyethylene Lauryl Ether | 1.90 |
| Polyoxyethylene Cholesteryl Ether | 2.00 |
| Water deionized | 16.35 |
| At room temperature, the following is added: 35% Hydrogen Peroxide | 41.30 |
| | 75.00 |

B. ALKALI METAL IODIDE COMPOSITION

| | Parts by Weight |
|---|---|
| Water | 16.40 |
| Potassium Iodide | 8.60 |
| | 25.00 |

The above ingredients are prepared in accordance with the procedure of Example I. A rich creamy foam is produced upon valve actuation containing approximately 3.0% free iodine.

EXAMPLE IV

A package is prepared in accordance with the procedure of Example I using the same ingredients and amounts set forth in Example III except 14% Hydrogen Peroxide (35% strength) is used with water to balance the amounts to 75 parts by weight for Composition A and 2.9% sodium iodide with the balance water to equal 25 parts by weight for Composition B.

The dispensed foamy product will contain about 1% free iodine.

Formulations of the present invention may also be devised which take advantage of the fact that hydrogen ions are involved in the oxidation of iodide ion to significantly increase the amounts of free iodine while simultaneously warming the end product. Such formulations incorporate between about 1 to 25 weight percent thermogenic agent selected from the group consisting of potassium, sodium and ammonium salts of thiosulfuric, thiocyanic, thioglycollic and sulfurous acids. The agents are preferably used in the presence of about one percent or less by weight of a catalyst selected from the group consisting of molydate, titanate, vanadate, and tungstate salts. Preferably sodium salts are utilized because of ready commercial availability.

Examples of the above formulations are as follows:

EXAMPLE V

A package for dispensing a warmed aerosol product is prepared in accordance with the procedure of Example I, except that Composition A includes the iodide salt with sodium thiosulfate agent in the presence of sodium molybdate catalyst.

COMPOSITION A

| | Parts by Weight |
|---|---|
| Sodium lauryl ether sulfate | 12.5 |
| Glycerin | 10.0 |
| Solulan 25 (solubilized lanolin derivative) | 5.0 |
| Sodium thiosulfate (anhydrous 100% basis) | 4.3 |
| Potassium iodide | 7.9 |
| Sodium molybdate | 0.1 |
| Triethanolamine | 6.0 |
| Oleic acid | 7.0 |
| Water, q.s. | 100.0 |

COMPOSITION B

| | Parts by Weight |
|---|---|
| Hydrogen Peroxide (100% basis) | 11.4 |
| Water, q.s. | 100.0 |

When mixed in a ratio of 3 parts Composition A to 1 part Composition B a rich antiseptic cleansing lather at about 35°C. above ambient temperature is dispensed from the previously described package. The cleansing lather will contain about three percent free iodine.

The following Examples produce substantially similar results and effects.

EXAMPLE VI

Example V is repeated using 2.2 parts of thiourea in place of the anhydrous sodium thiosulfate.

EXAMPLE VII

Example V is repeated using 2.7 parts of potassium thiocyanate in place of the anhydrous sodium thiosulfate.

EXAMPLE VIII

Example V is repeated using 2.9 parts of sodium thioglycollate in place of the anhydrous sodium thiosulfate.

EXAMPLE IX

Example V is repeated using 14.3 parts of sodium sulfate in place of the anhydrous sodium thiosulfate.

In the above Examples, the temperature of the end product may be raised or lowered as desired by raising or lowering the content of the thermogenic agent and peroxide content. For example, in Example V raising or lowering the sodium thiosulfate content in Composition A by 0.1 to 0.15 parts and peroxide content in Composition B by 0.25 to 0.38 parts for every degree centigrade, the temperature will be raised or lowered, respectively. In the case of Examples VI–IX, the thermogenic agents are raised or lowered in proportion to their weight ratio relative to the weight of sodium thiosulfate in Example V.

The invention has been described in terms of packages designed to liberate an iodine-containing foam for antiseptic purposes in which the liberated iodine is the sole antiseptic ingredient in the composition dispensed from the package. It will be apparent to one skilled in the art that additional active ingredients may be present in either or both compositions included within the pacakge to impart special therapeutic or other properties to the dispensed composition. For example, active antimicrobial ingredients such as hexachlorophene and quaternary ammonium compounds, for example, cetyl pyridinium chloride, benzalkonium chloride and the like can be included to yield compositions having good applicability to the treatment of such conditions as acne, dandruff and the like. Packages so formulated with additional ingredients are included within the scope of the invention.

The subject matter which the applicants regard as their invention is particularly pointed out and distinctly claimed as follows:

We claim

1. A package adapted for the dispensing of an antiseptic iodine-containing composition therefrom which comprises a pressure-tight container with means to maintain two ingredients therein isolated from each other, the first of said ingredients comprising about 2 – 50 weight percent of an alkali metal iodide selected from the group consisting of potassium iodide and sodium iodide and the second of said ingredients comprising about 2 – 30 weight percent hydrogen peroxide, a liquified gaseous propellant in at least one of said ingredients and valve means communicating with each of said ingredients adapted to mix effective portions of each of said ingredients to dispense from said package a heated composition containing free iodine.

2. A package according to claim 1 wherein said package is in aerosol form and wherein said liquified gaseous propellant is provided by including a liquified gas of the type used as an aerosol propellant in one of said ingredients contained within the main body portion of the container and wherein the other of said ingredients is contained within a separate compartment within said container separated from said first ingredient by a movable wall operable by a differential in pressure between said compositions upon actuation of said valve means, said liquified gas having a vapor pressure at 70°F. of between 12 and 85 pounds per square inch gauge.

3. A package according to claim 2 wherein said first ingredient comprises an aqueous solution of alkali metal iodide.

4. A package according to claim 3 wherein said means to apply pressure is provided by including a liquified propellant with said first and second ingredients, said liquified propellant having a vapor pressure at 70°F. of between 12 and 85 pounds per square inch gauge.

5. The package of claim 2 including with said first ingredient between about 1 to 25 weight percent of a thermogenic agent selected from the group consisting of potassium, sodium, and ammonium salts of thiosulfuric, thiocyanic, thioglycollic and sulfurous acids and about one percent or less by weight of a catalyst selected from the group consisting of sodium molybdate, sodium titanate, sodium vanadate, and sodium tungstate.

* * * * *